United States Patent [19]

Bellussi et al.

[11] Patent Number: 6,083,864
[45] Date of Patent: Jul. 4, 2000

[54] SYNTHETIC, CRYSTALLINE, POROUS MATERIAL CONTAINING OXIDES OF SILICON, TITANIUM AND GALLIUM

[75] Inventors: Giuseppe Bellussi, Piacenza; Mario Ga'briele Clerici, San Donato Milanese; Angela Carati, San Giuliano Milanese; Antonio Esposito, San Donato Milanese, all of Italy

[73] Assignee: Eniricerche S.p.A., Milan, Italy

[21] Appl. No.: 09/201,268

[22] Filed: Nov. 30, 1998

Related U.S. Application Data

[62] Division of application No. 08/738,734, Oct. 28, 1996, Pat. No. 5,888,471, which is a continuation of application No. 07/814,191, Dec. 20, 1991, abandoned, which is a continuation of application No. 07/660,249, Feb. 22, 1991, abandoned, which is a continuation of application No. 07/532,181, Jun. 1, 1990, abandoned, which is a continuation of application No. 07/110,926, Oct. 20, 1987, abandoned.

[30] Foreign Application Priority Data

Oct. 22, 1986 [IT] Italy ................................. 22 070 A/86

[51] Int. Cl.$^7$ ............................. B01J 29/40; B01J 29/88; B01J 29/89
[52] U.S. Cl. ................................. 502/61; 502/64; 502/73; 502/242; 502/263
[58] Field of Search ................................. 502/61, 64, 73, 502/242, 263

[56] References Cited

U.S. PATENT DOCUMENTS

| | | | |
|---|---|---|---|
| 3,702,886 | 11/1972 | Argauer et al. | 423/28 |
| 4,060,590 | 11/1977 | Whittam et al. | 423/328 |
| 4,410,501 | 10/1983 | Taramasso et al. | 423/326 |
| 4,585,641 | 4/1986 | Barri et al. | 423/331 |
| 4,623,530 | 11/1986 | Cullo et al. | 423/331 |
| 4,640,829 | 2/1987 | Rubin | 423/328 |
| 4,729,979 | 3/1988 | Zletz | 502/202 |
| 5,003,125 | 3/1991 | Giusti et al. | 585/530 |
| 5,246,690 | 9/1993 | Bellussi et al. | 423/705 |
| 5,365,002 | 11/1994 | Wallau et al. | 585/418 |
| 5,371,307 | 12/1994 | Guth et al. | 585/250 |

FOREIGN PATENT DOCUMENTS

| | | |
|---|---|---|
| 0107876 | 5/1984 | European Pat. Off. . |
| 266825 | 5/1988 | European Pat. Off. . |
| 2471950 | 6/1981 | France . |
| 3237389 | 4/1983 | Germany . |

*Primary Examiner*—Mark L. Bell
*Assistant Examiner*—David Sample
*Attorney, Agent, or Firm*—Hedman, Gibson & Costigan, P.C.

[57] ABSTRACT

A synthetic, crystalline, porous material is disclosed, together with the related preparation process. Such material of zeolitic nature containing oxides of silicon, titanium and gallium corresponds, in the calcined and anhydrous state, to the following empyrical formula:

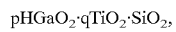

$$pHGaO_2 \cdot qTiO_2 \cdot SiO_2,$$

wherein p has a value greater than zero and smaller than or equal to 0.050, and q has a value greater than zero and smaller than or equal to 0.025, and the H$^+$ of HGaO$_2$ can be at least partially replaceable or replaced by cations.

5 Claims, 3 Drawing Sheets

SYNTHETIC, CRYSTALLINE, POROUS MATERIAL CONTAINING OXIDES OF SILICON, TITANIUM AND GALLIUM

This application is a divisional of application Ser. No. 08/738,734, filed on Oct. 28, 1996, now U.S. Pat. No. 5,888,471, which in turn is a continuation of application Ser. No. 07/814,191, filed on Dec. 20, 1991, now abandoned, which in turn is a continuation of application Ser. No. 07/660,249, filed Feb. 22, 1991, now abandoned, which in turn is a continuation of application Ser. No. 07/532,181, filed Jun. 1, 1990, now abandoned, which in turn is a continuation of application Ser. No. 07/110,926, filed Oct. 20, 1987, now abandoned.

The present invention relates to a synthetic material containing silicon, titanium and gallium oxides, having a porous, crystalline structure of zeolitic nature, and to the process for producing said material.

Such material is structurally similar to zeolite ZSM-5 disclosed in U.S. Pat. No. 3,702,886, formally constituted, in its calcined and anhydrous form, by $M_{2/n}O$, $SiO_2$, $Al_2O_3$ (wherein M=a cation of valence $\underline{n}$).

Other synthetic materials structurally correlated to zeolite ZSM-5 are known, such as that disclosed in U.S. Pat. No. 4,061,724, formally constituted, in its calcined and anhydrous form, by $SiO_2$ and that disclosed in BE-886,812, formally constituted, in its calcined and anhydrous form, by $SiO_2$ and $TiO_2$.

We have found now a novel synthetic zeolite, which we'll call as titanium-gallium-silicalite, structurally similar to silicalite, which can be used either as a molecular sieve, or as an ion-exchange material, or as a catalyst in the following reactions: cracking, selectoforming, hydrogenations and dehydrogenations, oligomerizations, alkylations, isomerizations, water removal from oxygen-containing organic compounds, selective oxidations and hydroxylations of organic substrates with $H_2O_2$ (e.g., oxidation of olefins, diolefins, alcohols, hydroxylations of aromatics, etc.).

The synthetic, crystalline, porous material of zeolitic nature of the present invention, containing oxides of silicon, titanium and gallium, meets, in its calcined and anhydrous state, the following empirical formula:

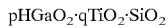

$pHGaO_2 \cdot qTiO_2 \cdot SiO_2$ wherein p has a value larger than zero and smaller than or equal to 0.050, and q has a value larger than zero and smaller than or equal to 0.025; and the $H^+$ of $HGaO_2$ can be at least partially replaceable, or replaced, by cations.

The passage from a cationic form to another cationic form can be carried out with the usual exchange processes known from the prior art.

The synthetic material in accordance with the present invention results crystalline when tested by X-ray examination.

Such examination was carried out by powder-diffractometer equipped with an electronic pulse counting system, using the CuK-alpha radiation. To compute the intensity values, the heights of the peaks were measured, and referred, as a percentage, to the most intense peak.

The main reflections for the calcined and anhydrous product are characterized by the following values of $\underline{d}$ (wherein $\underline{d}$ is the interplanar distance):

| d (Å) | Relative intensity |
| --- | --- |
| 11.14 ± 0.10 | vs |
| 9.99 ± 0.10 | s |
| 9.74 ± 0.10 | m |
| 6.36 ± 0.07 | mw |
| 5.99 ± 0.07 | mw |
| 4.26 ± 0.05 | mw |
| 3.86 ± 0.04 | s |
| 3.82 ± 0.04 | s |
| 3.75 ± 0.04 | s |
| 3.72 ± 0.04 | s |
| 3.65 ± 0.04 | m |
| 3.05 ± 0.02 | mw |
| 2.99 ± 0.02 | mw |

(wherein vs=very strong; s=strong; m=medium; mw=medium-weak).

Such a diffraction spectrum is essentially similar to that of ZSM-5, and, consequently, to the other zeolites which are structurally correlated to ZSM-5, which have been mentioned at the beginning of the present disclosure.

The material of the present invention shows an I.R. spectrum characterized by the following most representative values of $\underline{wn}$ (wherein $\underline{wn}$ is the wave number):

| wn (cm$^{-1}$) | Relative intensity |
| --- | --- |
| 1220–1230 | w |
| 1080–1110 | s |
| 965–975 | mw |
| 795–805 | mw |
| 550–560 | m |
| 450–470 | ms |

(wherein s=strong; ms=medium-strong; m=medium; mw=medium-weak; w=weak).

In FIG. 1, the I.R. spectrum is reported, wherein on the abscissa the wave number as cm$^1$ and on the ordinate the percent transmittance are reported.

Such I.R. spectrum is essentially similar to that of the zeolite disclosed in BE-886,812, and is considerably different from that of ZSM-5 (or from similar structures), shown in FIG. 2.

One can observe that in the spectrum the band at 965–975 cm$^{-1}$, characteristic of the titanium-silicalite of BE-886,812 and of titanium-gallium-silicalite is absent.

Summing-up, the herein disclosed material is different from ZSM-5 of U.S. Pat. No. 3,702,886, both due to its empirical formula, and due to its I.R. spectrum, and is different from the zeolite of BE-886,812 due to its empirical formula.

Furthermore, the use of the material of the present invention as a catalyst in the above listed reactions is a further confirmation of the difference of our product relatively to those known from the prior art.

In fact, ZSM-5 of U.S. Pat. No. 3,702,886 is used as a catalyst in such reactions as water removals from oxygen-containing organic compounds, cracking, selectoforming, hydrogenations and dehydrogenations, oligomerizations, alkylations, isomerizations, but results inactive in the reactions between organic substrates and $H_2O_2$ (hydroxylation of phenol to diphenols, oxidation of olefins, etc.), whilst the zeolite of BE-886,812 results to be inactive in the first reactions and active in the last reactions; on the contrary, the herein disclosed zeolite is active in all of the above-cited reactions.

A second object of the present invention is the process of preparation for obtaining the above disclosed synthetic, crystalline, porous material.

Said process is characterized in that under hydrothermal conditions a silicon derivative, a titanium derivative, a gallium derivative and a nitrogenous organic base are reacted, with a $SiO_2/Ga_2O_3$ molar ratio of the reactants larger than 100, preferably comprised within the range of from 150 to 600, an $SiO_2/TiO_2$ molar ratio of the reactants larger than 5, preferably comprised within the range of from 15 to 25, an $H_2O/SiO_2$ molar ratio of the reactants preferably comprised within the range of from 10 to 100, more preferably comprised within the range of 30 to 50, possibly in the presence of one or more alkali- and or alkali-earth-metal salts and/or hydroxides, with a molar $M/SiO_2$ ratio (wherein M is the alkali- and/or alkali-earth-metal cation) of the reactants smaller than 0.1, preferably smaller than 0.01, or equal to zero.

In the empirical formula of the material, gallium has been shown in the $HGaO_2$ form, to underline that the material is in H form. When the ratios between the various reactants are discussed, the gallium $Ga_2O_3$ form is used, in that it is more usual.

The silicon derivative is selected from silica gel, silica sol and alkylsilicates, among which tetraethylsilicate is the most preferred; the titanium derivative is selected from titanium salts, such as, e.g., titanium halides, and organic titanium derivatives, such as, e.g., alkyl-titanates, preferably tetraethyl-titanate; the gallium derivative is selected from its salts, such as, e.g., gallium halides, nitrates and hydroxides.

The nitrogenous organic base can be an alkyl-ammonium hydroxide, preferably tetrapropyl-ammonium hydroxide.

In case tetrapropyl-ammonium hydroxide is used, the $TPA^+/SiO_2$ ratio (wherein TPA=tetrapropyl-ammonium) of the reactants is comprised within the range of from 0.1 to 1, preferably of from 0.2 to 0.4. The reactants are reacted by operating at a temperature comprised within the range of from 100 to 200° C. At a pH comprised within the range of from 9 to 14, preferably of from 10 to 12, and for a time ranging from 1 hour to 5 days.

According to another form of practical embodiment of the present invention, titanium-gallium-silicalite can be in the form bonded with amorphous oligomeric silica, with an amorphous oligomeric silica/titanium-gallium-silicalite molar ratio comprised within the range of from 0.05 to 0.2, wherein the titanium-gallium-silicalite crystals are linked by Si—O—Si bridges, the mass of crystals of titanium-gallium-silicalite with silica being in the form of microspheres having a diameter comprised within the range of from 5 to 1000 μm.

The process for preparing the catalyst with the bonding agent is based on the use of an aqueous solution of silica and tetraalkyl-ammonium hydroxide, obtained by hydrolysing a tetraalkyl-silicate, preferably tetraethyl-orthosilicate, in an aqueous solution of tetraalkyl-ammonium hydroxide.

The alkyl radicals in the tetraalkyl-ammonium moiety contain a number of C atoms comprised within the range of from 1 to 5.

The hydrolysis is carried out in the liquid phase at a temperature comprised within the range of from room temperature to 200° C., and preferably within a time of from 0.2 to 10 hours.

In such a solution, silica is in an oligomeric form, and at high enough pH values, i.e., at a $pH \leq 10$.

When crystalline titanium-gallium-silicalite with very fine crystals is dispersed in this solution, the crystal surface is partly attacked by the alkalinity of the medium: such situation favours the formation of stable chemical bonds between the surface of the crystals and the oligomeric silicates in solution. By rapidly drying this suspension, by means of a spray-dryer, water is removed, and at the same time the crosslinking occurs of the oligomers, leading to the obtainment of microspheres formed by a tridimensional lattice wherein the zeolite crystallites are strictly linked by Si—O—Si bridges.

Before being used, the microspheres are calcined first under an inert medium ($H_2$, $N_2$, etc.), then they are oxidated at a temperature comprised within the range of from 150 to 700° C., preferably of from 500 to 600° C.

The optimum concentration of total solids ($SiO_2$, titanium-gallium-silicalite, TAA—OH) of the suspension to be atomized is of from 10% to 40% by weight. By varying the concentration of the solids in the suspension, or the dimensions of the atomizer, the average diameter of the obtained particles can be varied. The diameter of the catalyst microspheres can be thus varied within the range of from 5 to 10 μm, with the most suitable dimensions for any particular desired application being selected.

In order to better illustrate the meaning of the present invention, some preparation and application examples are hereunder reported, which anyway are not to be understood as being limitative of the same invention.

EXAMPLE 1

6.1 g of $Ga(NO_3)_3 \cdot 8H_2O$ is dissolved in 70 g of $C_2H_5OH$ and the so-obtained solution is added, with mild stirring, to a solution constituted by 22.7 g of tetraethyl-titanate and 416 g of tetraethyl-silicate.

The so-obtained clear alcoholic solution is added, with moderate stirring, to 870 g of an aqueous solution at 14% of tetrapropyl-ammonium hydroxide. The mixture is maintained stirred, while being possibly heated, until a single-phase, clear solution is obtained. Then, 700 g is added of demineralized water, with the mixture being stirred for a further hour. The obtained mixture is then charged to a stirred stainless-steel autoclave, and is heated, under its autogenous pressure, up to the temperature of 170° C. These conditions are maintained for 15 hours, the autoclave is then cooled and the reaction mixture is discharged. The obtained suspension is centrifuged and the solid is washed by re-dispersion and centrifuging, is dried at 120° C. and is then calcined at 550° C. for 4 hours.

The obtained product is then exchanged by the known processes into the protonic form.

The chemical analysis shows that the anhydrous product has the following composition;

$SiO_2/Ga_2O_3=195.5$;

$SiO_2/TiO_2=54.2$.

Figure 1:
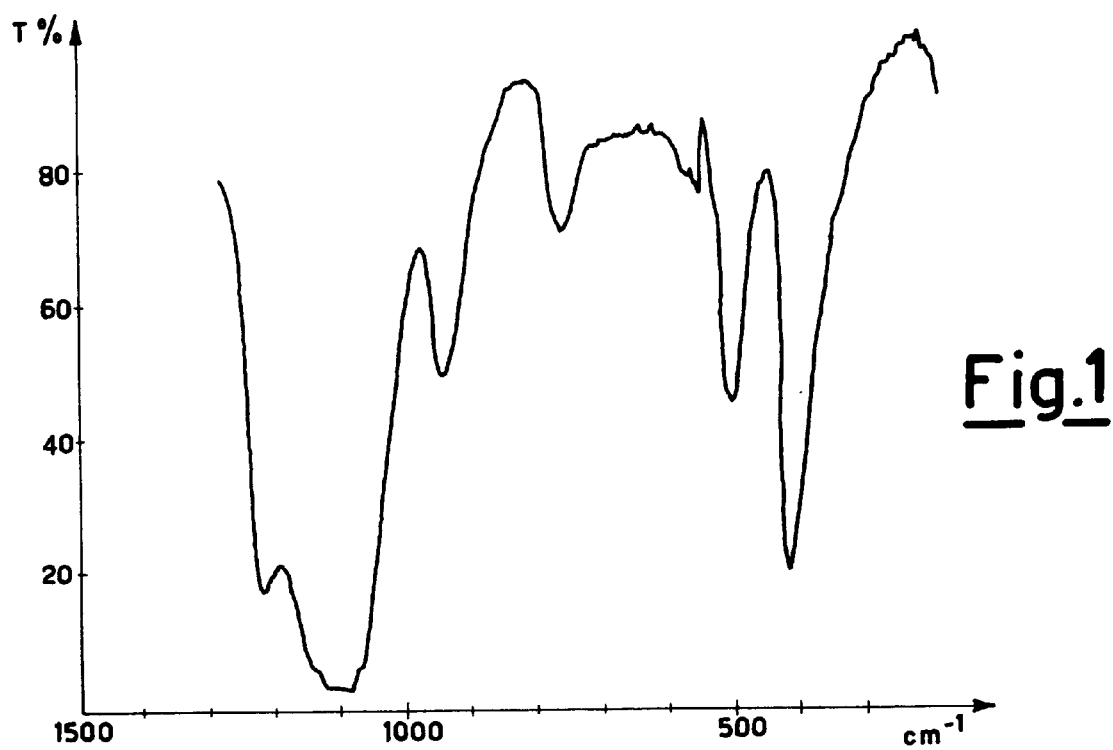
FIG. 1 is an IR spectrum of the crystalline porous material of the present invention.
Figure 2:
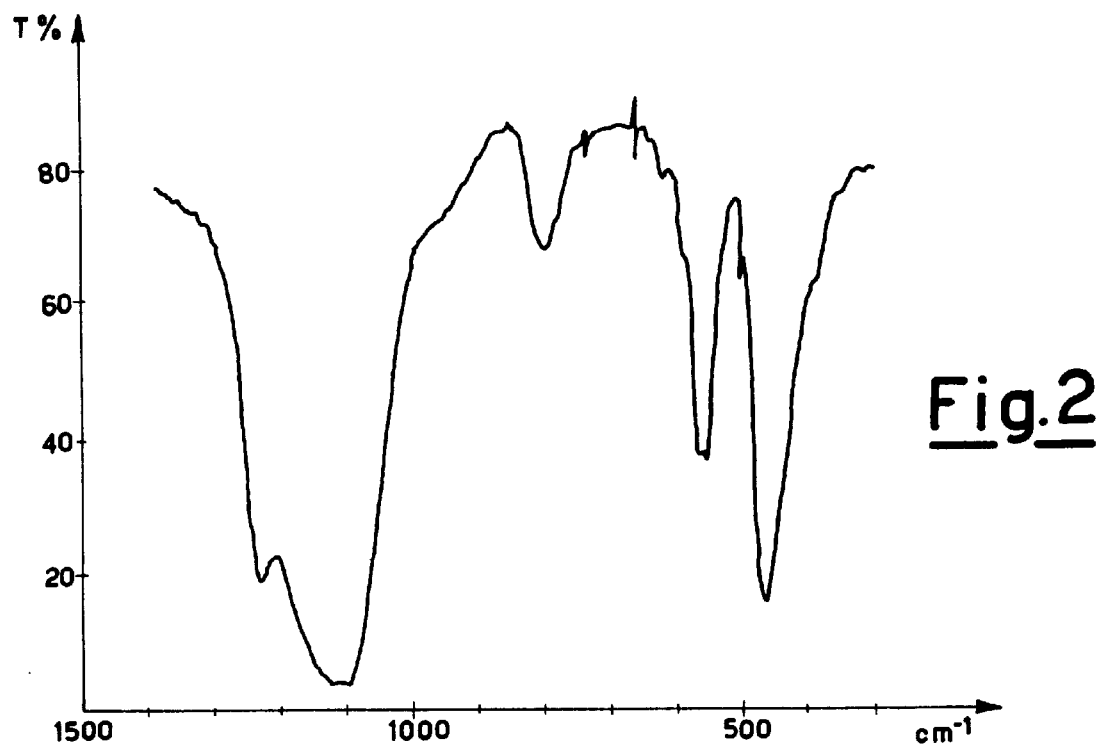
FIG. 2 is an IR spectrum of titanium silicate according to the prior art.
Figure 3:
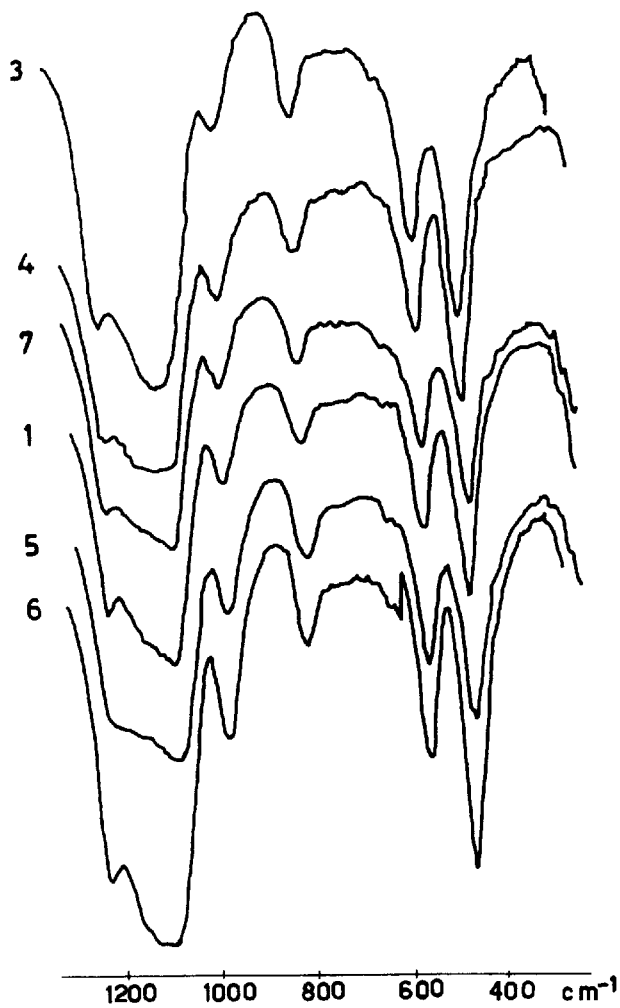
FIG. 3 is an IR spectra of the products of Examples 1 and 3–7.

The powder X-ray diffraction analysis shows that the product is crystalline, and has a ZSM-5-type structure. The I.R. spectrum thereof is shown in FIG. 3.

EXAMPLES 2–6

By the same modalities as of Example 1, five preparations are carried out, for which the molar compositions of the reactant mixtures and of the obtained products, as they result from the chemical analysis, are reported in Table 1.

In the Examples 3 and 6 crystallization times and temperatures have been modified. Particularly in Example 3 crystallization has been effected in 3 hours at 190° C. and in Example 6 in 5 days at 100° C.

The reaction mixture prepared as disclosed in Example 2 under the described conditions does not crystallize, but it remains as an amorphous product having a jelly consistency.

The products from Examples 3 through 6 are crystalline and the X-ray diffraction analysis shows that they are structures of ZSM-5 type.

The I.R. spectra are shown in FIG. 3.

EXAMPLE 7

By the same modalities of Example 1, a reaction mixture is prepared, which has the following molar ratios:

$SiO_2/TiO_2 = 20$
$SiO_2/Ga_2O_3 = 200$;
$TPA^+/SiO_2 = 0.3$;
$H_2O/SiO_2 = 40$.

The only difference consists in that gallium nitrate is directly dissolved in the solution at 14% of tetrapropyl-ammonium hydroxide, and not in ethyl alcohol. The reaction mixture is charged to the autoclave, and is left standing at 15 hours at 170° C. under its autogenous pressure. The discharged product is centrifuged and washed twice by re-dispersion and centrifugation, it is then dried one hour at 120° C. and is then calcined 4 hours at 550° C. in air.

The product obtained in the calcined and anhydrous form has the following chemical composition:

$SiO_2/TiO_2 = 38.2$;
$SiO_2/Ga_2O_3 = 140$.

The powder X-ray diffraction analysis shows the presence of a crystalline structure of ZSM-5 type, and of traces of crystalline $TiO_2$ (anatase).

In FIG. 3, the I.R. spectra are reported of the gallium-titanium-silicalites of Examples 1 and 3 through 7.

Figure 4:
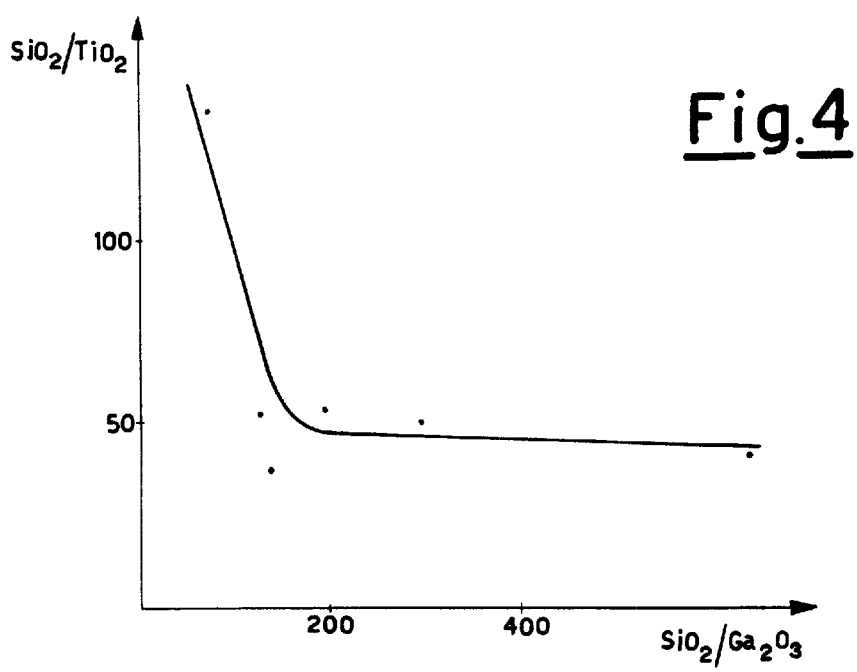
FIG. 4 shows the decrease in $SiO_2/TiO_2$ ratio with increasing $SiO_2/Ga_2O_3$ ratio.

From FIG. 4, it can be seen how the $SiO_2/TiO_2$ ratio in the obtained product decreases with increasing $SiO_2/Ga_2O_3$ ratio, until it stabilizes around a value of 40–50 for an $SiO_2/Ga_2O_3$ ratio larger than 200.

Figure 5:
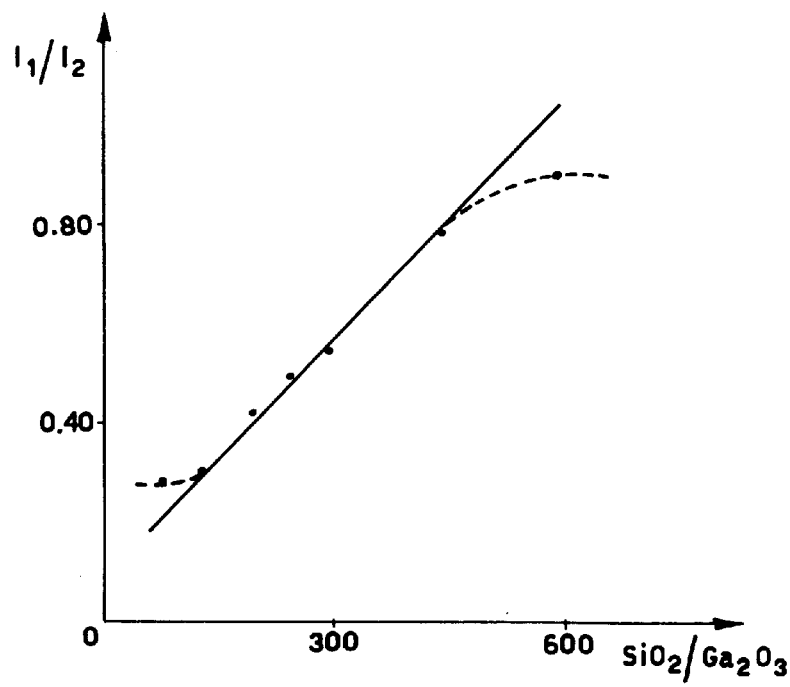
FIG. 5 shows the variation of the relative intensity between the band associated with structural titanium and the band associated with silicalite, at the increasing of the ratio $SiO_2/Ga_2O_3$.

From FIG. 5, it can be seen how in the I.R. spectrum the value varies of the relative intensity ratio between the band at 970 $cm^{-1}$ ($I_1$), attributed to structural titanium, and a silicalite band at 550 $cm^{-1}$.

Such an intensity ratio increases with increasing $SiO_2/Ga_2O_3$ ratio and this fact indicates that titanium in the crystalline lattice actually increases with decreasing gallium.

Figure 6:
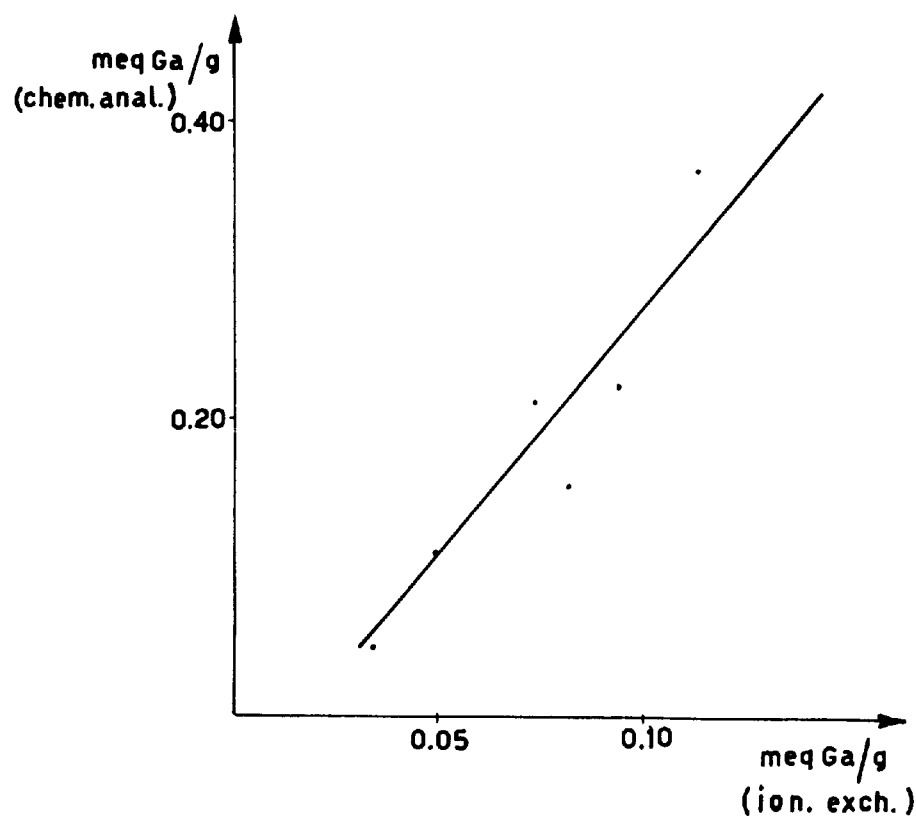
FIG. 6 shows the increase in exchange capacity of the porous material of the present invention with increase in gallium content.

From FIG. 6, it can be seen how with increasing values of gallium found in the chemical analysis, the exchange capacity of the obtained zeolite increases; this demonstrates that gallium found on chemical analysis is really structural gallium.

EXAMPLE 8

In this Example, the preparation is shown of the catalyst of Example 1 with a bonding agent.

100 g of $Ga(NO_3)_3 \cdot 8H_2O$ is dissolved in 1,050 g of $C_2H_5OH$ and the so-obtained solution is added, with mild stirring, to a solution constituted by 340.5 g of tetraethyl-titanate and 6,240 g of tetraethyl-silicate.

The so-obtained clear alcoholic solution is added, with moderate stirring, to 13,000 g of an aqueous solution at 14% of tetrapropyl-ammonium hydroxide. The mixture is maintained stirred, while being possibly heated until a single-phase, clear solution is obtained. Then, 10,500 g is added of demineralized water, with the mixture being kept stirred for a further hour. The resulting mixture is then charged to a stirred stainless-steel autoclave, and is heated, under its autogenous pressure, up to the temperature of 170° C. These conditions are maintained for 15 hours, the autoclave is then cooled and the reaction mixture is discharged. The obtained suspension is centrifuged and the solid is washed by re-dispersion and centrifuging.

550 g of tetraethyl-silicate is added with stirring to 590 g of an aqueous solution of tetrapropyl-ammonium hydroxide at 12%, and the resulting mixture is stirred for approximately 60° C. for 1 hour; then, 2,400 g of demineralized water is added, and the solution is kept stirred a further hour, while being made cool down to approximately 25° C.

Into the so-obtained clear solution, 2,050 g is carefully dispersed of the washed centrifugation cake, prepared as disclosed above. The centrifugation cake contains approximately 70% by weight of zeolite.

The resulting milky suspension is fed to a spray-dryer (NIRO-ATOMIZER; disk-atomized; inlet air temperature 300° C.; outlet air temperature 120° C.; chamber diameter 1.5 m), compact microspheres being obtained, which have an average diameter close to 20 μm.

The atomized product is heated to 550° C. under a $N_2$ atmosphere; the atmosphere is gradually turned from $N_2$ into air, and the product is maintained a further two hours at 550° C. in air.

The obtained solid has the following composition, expressed as molar ratios:

$SiO_2/Ga_2O_3 = 217$;
$SiO_2/TiO_2 = 60$.

EXAMPLE 9

4 g of catalyst according to Example 4 and 60 ml of 1-octene are charged to a glass autoclave and are then heated to the temperature of 200° C., with stirring, for 5 hours. After cooling, the suspension is filtered and the products are analyzed by gas-chromatography and mass spectrometry.

1-Octene conversion: 18%
Selectivity to dimers: 95%
Selectivity to trimers 5%

EXAMPLE 10

To a steel autoclave of 1 litre capacity, equipped with mechanical stirrer and temperature control system, 373 g of methanol, 4 g of catalyst according to Example 8, 5.0 g of benzene (as the internal standard for gas-chromatographic analysis) and 45 g of 1-butene are charged. After adjusting the temperature at the controlled value of 22° C., to the suspension of 20 ml of hydrogen peroxide at 33% (w/v) is added with intense stirring. The reaction is monitored by drawing samples for analysis and filtering them. Hydrogen peroxide is measured by iodometric titration, and the reaction products are measured by GLC, with an 1.8-metre long column packed with Poropak PS. Forty-five minutes later the situation is as follows:

| Converted $H_2O_2$ | 85% |
|---|---|
| 1,2-Epoxybutane | 0.0326 mol |
| 1-Methoxy-2-hydroxybutane | 0.0795 mol |
| 2-methoxy-1-hydroxybutane | 0.0517 mol |

EXAMPLE 11

To an autoclave of 1 litre of capacity, equipped with mechanical stirrer, temperature control system, and constant pressure control system, 193 g of methanol, and 4.0 g of catalyst according to Example 4 are charged. To a vessel connected with the autoclave, 11.2 g of $H_2O_2$ at 32% (w/w) is charged. After adjusting the temperature to the controlled value of 22° C., and pressurizing with propylene, with stirring, at 300 kPa (with this pressure being kept constant during the whole reaction time), to the suspension inside the autoclave all hydrogen peroxide is added at a time.

The reaction is monitored by drawing samples of suspension, which are filtered and analyzed. Hydrogen peroxide is measured by iodometric titration, and the reaction products are measured by gas-chromatography on an 1.8-metre long column packed with Poropak PS. After 45 minutes, the situation is as follows:

| Converted $H_2O_2$ | 88% |
|---|---|
| Propylene oxide | $6.02 \times 10^{-3}$ mol |
| 1-Methoxy-2-hydroxypropane | $52.0 \times 10^{-3}$ mol |
| 2-methoxy-1-hydroxypropane | $34.6 \times 10^{-3}$ mol |

EXAMPLE 12

To a small glass flask of 250 cc of capacity, in the following order: phenol, 99.8 g; water, 24.2 g; acetone, 18,5 g; catalyst, prepared as per Example 5, 5 g; are charged.

The reaction mixture is heated to 100° C., with stirring, and refluxing; then, under the same conditions, within a 45-minute time 15.4 g of $H_2O_2$ at 60% w/w is added dropwise.

Sixty minutes after the beginning of the addition, all $H_2O_2$ has been converted, and the reaction products are analyzed by gas-chromatography.

A yield of diphenols of $$\text{yield} = \frac{\text{obtained diphenol mol}}{\text{charged } H_2O_2 \text{ mol}} \times 100 = 74.7\%$$

is obtained.

The residual amount of $H_2O_2$ is converted into pitches and $O_2$. In the obtained diphenols, the ortho/para ratio is 1.26.

TABLE 1

| | Composition of the Reaction Mixture | | | | Product Composition | |
|---|---|---|---|---|---|---|
| Example | $SiO_2/$ $TiO_2$ | $SiO_2/$ $Ga_2O_3$ | $TPA^+/$ $SiO_2$ | $H_2O/$ $SiO_2$ | $SiO_2/$ $TiO_2$ | $SiO_2/$ $Ga_2O_3$ |
| 1 | 20 | 250 | 0.3 | 40 | 54.2 | 195.5 |
| 2 | 20 | 50 | 0.3 | 40 | Not crystallized | |
| 3 | 20 | 80 | 0.3 | 40 | 135.5 | 79.2 |
| 4 | 20 | 130 | 0.3 | 40 | 53.3 | 128.8 |
| 5 | 20 | 300 | 0.3 | 40 | 50.9 | 294.1 |
| 6 | 20 | 600 | 0.3 | 40 | 43.5 | 641.7 |

What is claimed is:

1. A process for the preparation of a catalyst based on silicon, titanium and gallium, wherein said catalyst is in the form of microspheres and comprises oligomeric silica and crystals of a synthetic, crystalline, porous material comprising oxides of silicon, titanium and gallium, having the following formula, in its calcinated and anhydrous state:

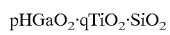

$$pHGaO_2 \cdot qTiO_2 \cdot SiO_2$$

wherein p is a value larger than zero and smaller than or equal to 0.050, q is a value larger than 0 and smaller than or equal to 0.025, and the $H^+$ of $HGaO_2$ can be at least partially replaced by cations, the material exhibiting an X-ray diffraction spectrum of

| d | $I_{rel}$ |
|---|---|
| 11.14 ± 0.10 | vs |
| 9.99 ± 0.10 | s |
| 9.74 ± 0.10 | m |
| 6.36 ± 0.07 | mw |
| 5.99 ± 0.07 | mw |
| 4.26 ± 0.05 | mw |
| 3.86 ± 0.04 | s |
| 3.82 ± 0.04 | s |
| 3.75 ± 0.04 | s |
| 3.72 ± 0.04 | s |
| 3.65 ± 0.04 | m |
| 3.05 ± 0.02 | mw |
| 2.99 ± 0.02 | mw | wherein d is the interplanar distance, expressed as Å, and $I_{rel}$ is the relative intensity, wherein vs means very strong, s means strong, m means medium, and mw means medium weak, and the material exhibiting an I.R. spectrum having at least the following bands:

| wn | $I_{rel}$ |
|---|---|
| 1220–1230 | w |
| 1080–1110 | s |
| 965–975 | mw |
| 795–805 | mw |
| 550–560 | m |
| 450–470 | ms | wherein wn is the wave number, as $cm^{-1}$, and $I_{rel}$ is the relative intensity, wherein s means strong, ms means medium-strong, m means medium, mw means medium weak and w means weak, said synthetic, crystalline, porous material being produced by reacting under hydrothermal conditions a silicon derivative, a titanium derivative, a gallium derivative, a nitrogenous organic base and one or more alkali or alkali-earth metal salts and/or hydroxides having an alkali or alkali-earth metal cation M with a $SiO_2/Ga_2O_3$ molar ratio of the reactants larger than 100, a $SiO_2/TiO_2$ molar ratio of the reactants larger than 5 and a $M/SiO_2$ molar ratio of the reactants smaller than 0.1 or equal to zero wherein M is an alkali and/or alkali-earth metal cation; with an oligomeric silica/titanium-gallium-silicalite molar ratio comprised within the range of from 0.05 to 0.2, wherein the crystals of titanium-gallium-silicalite are linked with one another by means of Si—O—Si bridges, said process characterized in that in an aqueous solution of silica and tetraalkyl-ammonium hydroxide, obtained by hydrolyzing in the liquid phase a tetraalkyl-orthosilicate in an aqueous solution of tetraalkyl-ammonium hydroxide at a temperature comprised within the range of from room temperature to 200° C. and for a time comprised within the range of from 0.2 to 10 hours, titanium-gallium-silicalite crystals are dispersed, a suspension of titanium-gallium-silicalite and oligomeric silica being obtained, and the obtained suspension is submitted to a fast drying.

2. Process according to claim 1, wherein the tetraalkyl-orthosilicate is tetraethyl-orthosilicate.

3. Process according to claim 1, wherein the hydrolysis is carried out at a temperature comprised within the range of from 40 to 100° C.

4. Process according to claim 1, wherein the tetraalkyl-ammonium has its alkyls with a number of carbon atoms within the range of from 1 to 5.

5. Process according to claim 4, wherein the tetraalkyl-ammonium is tetrapropyl-ammonium.

* * * * *

UNITED STATES PATENT AND TRADEMARK OFFICE
CERTIFICATE OF CORRECTION

PATENT NO. : 6,083,864
DATED : July 4, 2000
INVENTOR(S) : Giuseppe Bellussi et al.

It is certified that error appears in the above-identified patent and that said Letters Patent is hereby corrected as shown below:

Title Page, item [73] Assignee: Should read as follows:

Eniricerche S.p.A., Milan, Italy
Enichem Synthesis S.p.A., Palermo, Italy
Snamprogetti S.p.A., Milan, Italy Signed and Sealed this Thirty-first Day of October, 2000

Attest:

Q. TODD DICKINSON

*Attesting Officer*                *Director of Patents and Trademarks*